United States Patent [19]
Moriya

[11] Patent Number: 5,808,744
[45] Date of Patent: Sep. 15, 1998

[54] APPARATUS FOR INSPECTING REPETITIVE PATTERNS

[75] Inventor: Kazuo Moriya, Ageo, Japan

[73] Assignee: Mitsui Mining & Smelting Co., Ltd., Tokyo, Japan

[21] Appl. No.: 794,390

[22] Filed: Feb. 6, 1997

[30] Foreign Application Priority Data

Feb. 16, 1996 [JP] Japan ................................. 8-052533

[51] Int. Cl.$^6$ .......................... G01N 21/00; G01B 11/00; H04N 7/18
[52] U.S. Cl. ................... 356/394; 356/237; 250/559.39; 250/559.4; 348/126; 348/132; 382/145
[58] Field of Search .................................. 356/394, 390, 356/237, 239; 348/131–132, 87, 94–95, 126, 129–130; 250/559, 39, 40, 44, 46; 382/147, 149, 151

[56] References Cited

U.S. PATENT DOCUMENTS

| 4,305,658 | 12/1981 | Yoshida ..................................... | 356/23 |
| 4,486,776 | 12/1984 | Yoshida ..................................... | 356/23 |
| 4,864,631 | 9/1989 | Jensen ................................. | 250/559.44 |
| 4,896,211 | 1/1990 | Hunt et al. ............................... | 358/106 |
| 5,457,490 | 10/1995 | Doane ..................................... | 348/132 |
| 5,581,074 | 12/1996 | Yoshida ..................................... | 348/132 |

FOREIGN PATENT DOCUMENTS 63-015380  1/1988  Japan .

Primary Examiner—Frank G. Font
Assistant Examiner—Jason D. Vierra-Eisenberg
Attorney, Agent, or Firm—Kubovcik & Kubovcik

[57] ABSTRACT

An apparatus for inspecting repetitive patterns includes a signal generation device for outputting a signal every time each of repetitive patterns reaches a predetermined observation area, and a flash generation device for generating a flash in synchronism with the signal to instantaneously illuminate each of the patterns sequentially reaching the observation area. The signal generation device may be a device for generating a signal upon detecting the predetermined shape of each pattern. The repetitive patterns may be those on a tape carrier which moves, e.g., in the longitudinal direction thereof. It is preferable to provide an image pickup device for picking up the image of each repetitive pattern on the observation area and a display device for displaying the picked-up image. The display device preferably keeps display of the picked-up image of each of the patterns illuminated by the flash for a predetermined period of time within between this illumination and the next illumination by the next flash.

11 Claims, 2 Drawing Sheets

APPARATUS FOR INSPECTING REPETITIVE PATTERNS

BACKGROUND OF THE INVENTION

1. Field of the Invention

The present invention relates to an apparatus for inspecting repetitive patterns and more particularly to an apparatus adapted to inspect repetitive patterns on a tape carrier (hereinafter referred to as a TAB tape) for use in bonding semiconductor chips to detect abnormality in the repetitive patterns if any.

2. Prior Art

Visual inspection of such a TAB tape in its manufacturing process is conventionally performed while the TAB tape remains stationary.

SUMMARY OF THE INVENTION

If the TAB tapes can be inspected while moving them in the manufacturing line of the TAB tapes, however, their production efficiency can be improved.

It is therefore an object of the present invention to provide an apparatus capable of inspecting a TAB tape moving on its manufacturing line without stopping the movement of the TAB tape.

In order to achieve the above object, there is provided an apparatus for inspecting repetitive patterns which comprises signal generation means for outputting a signal every time each repetitive pattern reaches a predetermined observation area, and flash generation means for generating a flash in synchronism with the signal to instantaneously illuminate each pattern sequentially reaching the observation area.

With this arrangement, each repetitive pattern is instantaneously illuminated every time it reaches the observation area. Thus, each pattern sequentially reaching the observation area is deemed to be substantially stop at the same position and a plurality of normal patters are superposed to enable their images to be observed as a single pattern. Each pattern can be visually and easily compared with its adjacent patterns and, if a pattern which partially differs from other patterns due to some abnormality is illuminated in the observation area, the different portion is observed as if it were moving whereby the abnormality is instantaneously detected.

The signal generation means generates a signal upon detecting a predetermined shape on the pattern. When a TAB tape is to be inspected, repetitive patterns such as device holes or inner leads on the TAB tape which moves in its longitudinal direction are observed as the predetermined shape. In this case, it is preferable to arrange image pickup means for picking up the image appearing at the observation area and display means for monitoring the image appearing at the observation area. In addition, the display means preferably keeps displaying one pattern illuminated by a flash for a predetermined period of time within between this illumination and the next illumination by the next flash. Even when the image which is instantaneously displayed on the display means is visually observed, a change in pattern can be recognized because its afterimage remains on the retina for a certain period of time; however, when one pattern is kept displayed on the display means until the adjacent pattern is displayed, a change in pattern can be more easily recognized.

BRIEF DESCRIPTION OF TILE DRAWINGS

DESCRIPTION OF THE PREFERRED EMBODIMENT

Figure 1:
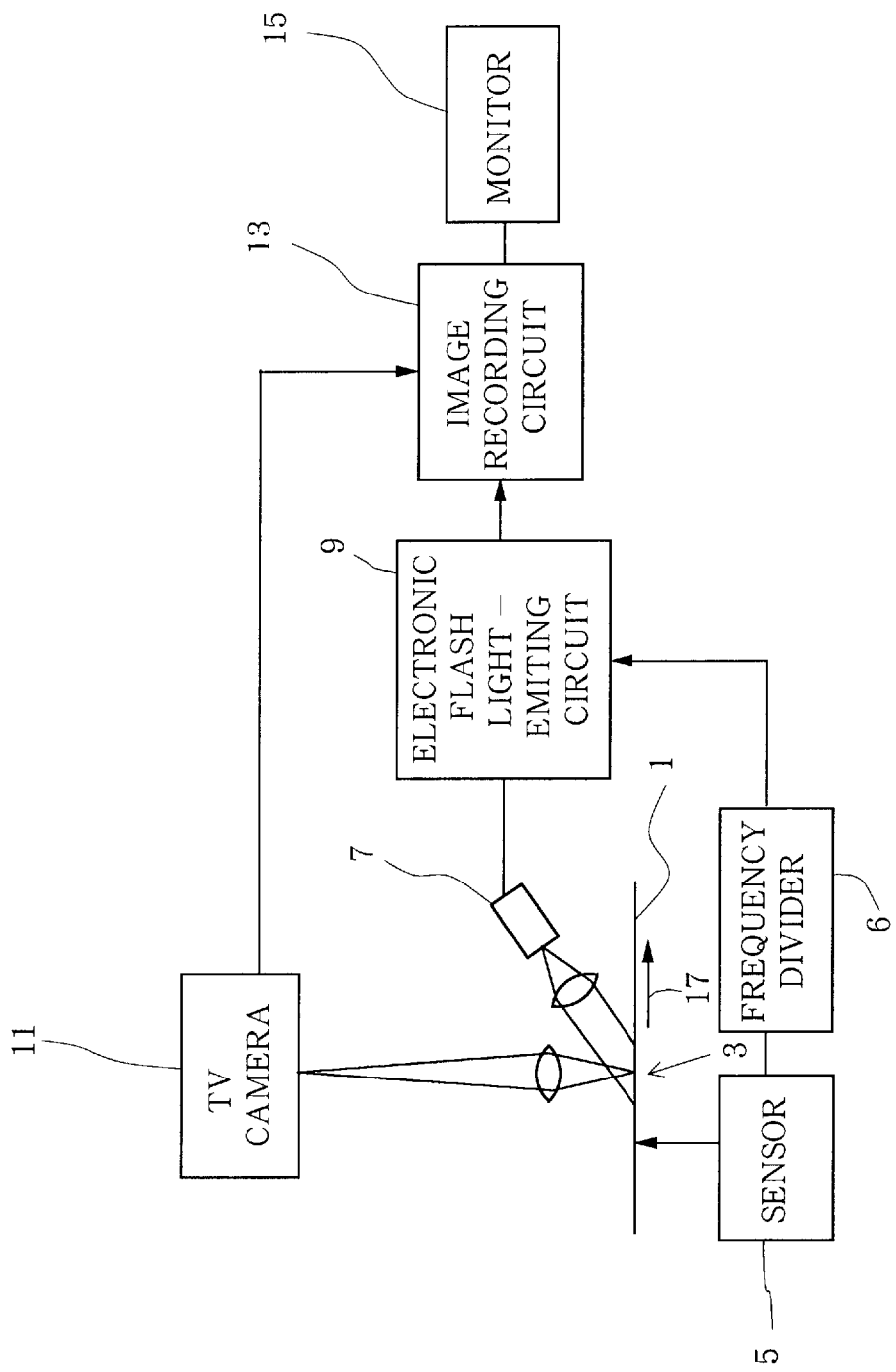
FIG. 1 is a block diagram showing a TAB tape inspection apparatus according to an embodiment of the present invention.

FIG. 1 is a block diagram showing a TAB tape inspection apparatus according to an embodiment of the present invention. As shown in FIG. 1, this apparatus comprises signal generation means (5 and 6) for detecting a predetermined shape on each repetitive pattern on a TAB tape 1 every time each pattern reaches an observation area 3 thereby outputting a signal, an electronic flash light-emitting device 7 and electronic flash light-emitting circuit 9 which generate a flash in synchronism with the signal to instantaneously illuminate each pattern sequentially reaches the observation area 3, a TV camera 11 for sensing each pattern on the observation area 3, an image recording circuit (e.g. memory means) 13 for storing the image data, sent from the TV camera 11, of each pattern illuminated with the flash for a predetermined period of time within between this illumination and the next illumination by the next flash, and a monitor 15 for displaying the image data stored in the image recording circuit 13.

Figure 2:
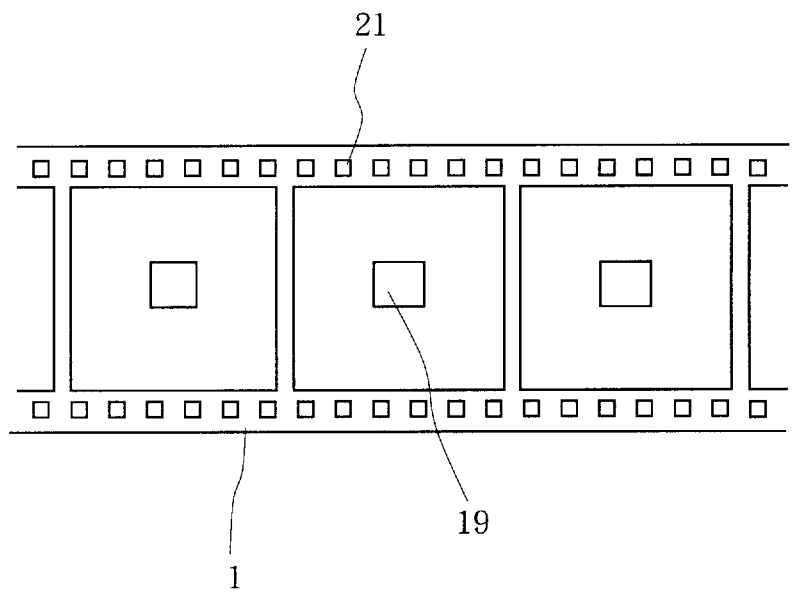
FIG. 2 is a view showing part of a TAB tape.

FIG. 2 shows part of the TAB tape 1. Referring to FIG. 2, reference numeral 19 denotes each device hole where inner leads to be bonded with a semiconductor chip are projected; and 21, each sprocket hole formed in the TAB tape 1. As shown in FIG. 2, the TAB tape 1 has repetitive patterns. Since the TAB tape 1 is provided with the sprocket holes 21 for passing the tape forward, the repetitive patterns usually respectively reach the observation area every time a predetermined number, n, of sprocket holes are passed, n being 6 in case of FIG. 2.

The signal generation means has a sensor 5 having both a light-emitting device and a light-receiving device to detect the sprocket holes 21, and a frequency divider 6 for outputting a signal representing that a pattern reaches the observation area 3 as a trigger signal to the electronic flash light-emitting circuit 9 on the basis of a detection signal from the sensor 5. The frequency divider 6 outputs a trigger signal every time the sensor 5 detects the predetermined number, n, of the sprocket holes. The electronic flash light-emitting circuit 9 drives the electronic flash light-emitting device 7 in accordance with this trigger signal to emit light and also outputs a trigger signal for image recording to the image recording circuit 13. The image recording circuit 13 receives an image signal from the TV camera 11 in accordance with this trigger signal and simultaneously updates the recorded contents.

A sensor for detecting the device hole 19 may also be provided, and a trigger signal to the electronic flash light-emitting circuit 9 may be generated on the basis of an output from this sensor and the output from the sensor 5.

With the above arrangement, every time the sensor 5 of the signal generation means detects the predetermined number, n, of the sprocket holes 21 of the TAB tape 1 which is traveling in the direction indicated by an arrow 17 through the observation area 3, i.e., every time each repetitive pattern of the TAB tape 1 reaches the observation area 3, the frequency divider 6 of the signal generation means sends a trigger signal to the electronic flash light-emitting circuit 9. The electronic flash light-emitting circuit 9 outputs a light-emitting instruction to the electronic flash light-emitting device 7 in accordance with this trigger signal. The electronic flash light-emitting device 7 emits a flash in accordance with this instruction, thereby illuminating each repetiting pattern sequentially reaching the observation area. In synchronism with this illumination, the image recording circuit 13 repeats records of image data from the TV camera 11 in accordance with the trigger signal from the electronic flash light-emitting circuit 9. The image data are overwritten and updated every time.

The traveling speed of the TAB tape 1 is, e.g., 30 to 80 [mm/sec], and the period of time for which the flash light-emission effected by the light-emitting device 7 is kept one time, is about 10 [$\mu$·sec]. The TAB tape 1 travels about 1 $\mu$m during the light-emitting period of time. The image of each pattern with this image blur is sensed by the TV camera 11, and recorded and updated in the image recording circuit 13. Therefore, the repetitive patterns substantially in the stationary state are displayed on the monitor 15 one after another. If a pattern whose wiring pattern or bonding state has a defective portion reaches the observation area 3, a partial change in pattern shape is confirmed through the monitor 15 before the next pattern is displayed, thereby to detect the defect.

Figure 3:
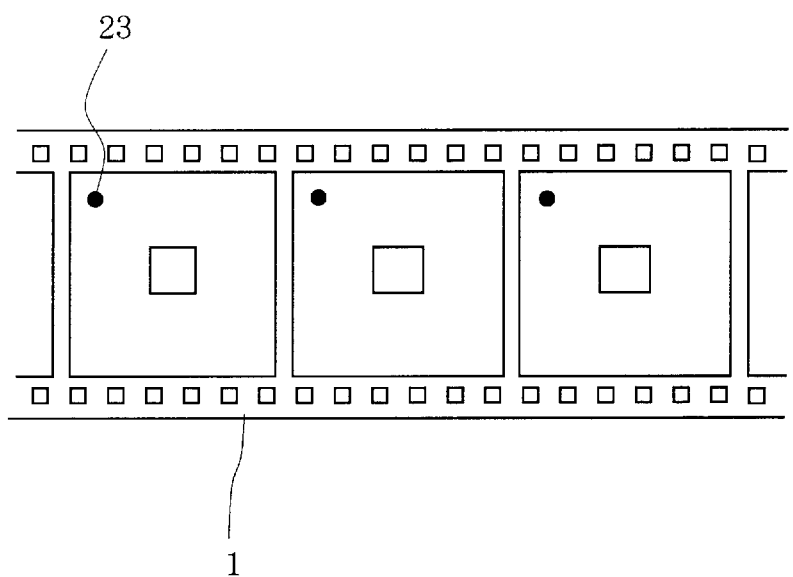
FIG. 3 is a view showing a TAB tape with marks.

Instead of detecting the sprocket holes 21, a mark or hole 23 as shown in FIG. 3, which is formed in each pattern on the TAB tape 1 in advance, may be detected to generate a trigger signal to the electronic flash light-emitting circuit 9. In this case, no frequency divider is needed. Alternatively, lead frames or the like may be detected.

In the above embodiment, visual inspection is performed by observing the monitor 15. Instead, image data in the image recording circuit 13 may be subjected to image processing and inspected.

According to the present invention, an abnormality in each of the repetitive patterns moving through the observation area can be efficiently inspected with a relatively simple arrangement. In addition, the TAB tape can be inspected without stopping or suspending the production line.

What is claimed is:

1. An apparatus for use in visually inspecting repetitive patterns each of which reaches a predetermined observation area sequentially, comprising:

wherein the repetitive patterns are those formed on a tape carrier for use in bonding a semiconductor chip, which moves in the longitudinal direction thereof;

signal generation means for outputting a signal every time each of said repetitive patterns reaches said observation area;

flash generation means for generating a flash in synchronism with the signal to instantaneously illuminate each of the patterns sequentially reaching the observation area further comprising an image pickup means for picking up the image of each of the patterns sequentially reaching the observation area and display means for displaying each of the picked-up images to monitor the images for determining if an abnormal pattern is passing through the observation area when at least a portion of the image changes.

2. An apparatus according to claim 1, wherein said signal generation means generates the signal upon detecting a predetermined shape on the pattern.

3. An apparatus according to claim 1, further comprising an image recording means for causing said display means to keep display of the picked-up image of each of the patterns illuminated by the flash for a predetermine period of time within this illumination and the next illumination by the next flash.

4. An apparatus according to claim 1, wherein said signal generation means has a sensor for detecting sprocket holes on said tape carrier, and a frequency divider for outputting a signal every time said sensor detects a predetermined number of sprocket holes.

5. An apparatus according to claim 1, wherein said signal generation means has a sensor for detecting a mark formed per device hole on said tape carrier and generates a signal every time the mark is detected.

6. An apparatus according to claim 1, wherein said signal generation means generates the signal upon detecting a predetermined shape on the pattern.

7. An apparatus according to claim 1, further comprising image pickup means for picking up the image of each of the patterns sequentially reaching the observation area and display means for displaying each of the picked-up images to monitor the images.

8. An apparatus according to claim 7, further comprising an image recording means for causing said display means to keep display of the picked-up image of each of the patterns illuminated by the flash for a predetermined period of time within this illumination and the next illumination by the next flash.

9. A method for inspecting repetitive patterns, comprising:

moving a carrier tape on which repetitive patterns to be inspected are formed through a predetermined observation area;

instantaneously illuminating each of the patterns sequentially reaching the observation area in synchronism with an arrival of each pattern at a predetermined position in the observation area by a flash;

visually watching an image appearing at the observation area; and determining that the patterns sequentially passing through the observation area are normal when the image substantially stops and that an abnormal pattern is passing through the observation area when at least a portion of the image changes.

10. A method according to claim 9, wherein images of the patterns sequentially reaching the observation area are picked up with an image pickup means and superposed on each other on a display means such that a plurality of normal images are displayed as a single image.

11. A method according to claim 10, wherein said display means comprises an image recording means for keeping display of the picked-up image of each of the patterns illuminated by the flash for a predetermined period of time within this illumination and the next illumination by the next flash.

* * * * *